United States Patent [19]
Weinstein et al.

[11] 3,931,046
[45] Jan. 6, 1976

[54] V-P-ZR CATALYSTS AND METHOD OF PREPARATION THEREOF IN THE ABSENCE OF HYDROGEN HALIDE

[75] Inventors: Benjamin Weinstein, Morganville; Anthony T. Jurewicz; Lewis Brewster Young, both of Kendall Park, all of N.J.

[73] Assignee: Mobil Oil Corporation, New York, N.Y.

[22] Filed: Apr. 17, 1974

[21] Appl. No.: 461,667

[52] U.S. Cl............ 252/429 R; 252/428; 252/435; 252/437; 260/346.8 A
[51] Int. Cl.²........................................ B01J 27/18
[58] Field of Search.. 260/346.8 A; 252/428, 429 R, 252/430, 435, 437

[56] References Cited
UNITED STATES PATENTS

| | | | |
|---|---|---|---|
| 2,773,921 | 12/1956 | Rylander et al. | 252/435 X |
| 3,156,705 | 11/1964 | Kerr | 252/437 X |
| 3,293,268 | 12/1966 | Bergman et al. | 252/437 X |
| 3,684,741 | 8/1972 | Friedrichsen et al. | 252/437 X |
| 3,832,359 | 8/1974 | Freerks et al. | 252/437 X |

Primary Examiner—Patrick P. Garvin
Attorney, Agent, or Firm—Charles A. Huggett; Hastings S. Trigg

[57] ABSTRACT

V-P-Zr catalysts having good activity and selectivity and high physical strength for the oxidation of alkanes, cycloalkanes and mixtures rich in them to dicarboxylic acid anhydrides (e.g. maleic anhydride) are prepared by refluxing an aqueous mixture of vanadium pentoxide and lower dialkyl phosphonate, adding a zirconium salt, and then adding phosphoric acid.

4 Claims, No Drawings

V-P-ZR CATALYSTS AND METHOD OF PREPARATION THEREOF IN THE ABSENCE OF HYDROGEN HALIDE

CROSS-REFERENCE TO RELATED APPLICATIONS

This application is related to copending application Ser. No. 461,777 filed concurrently herewith, now U.S. Pat. No. 3,888,886 which describes catalysts comprising complex reaction products of a vanadium oxy salt and phosphoric acid promoted with certain metals, and which is a continuation-in-part of Ser. No. 379,667, filed July 16, 1973, now abandoned which is a continuation-in-part of Ser. No. 261,030, filed June 8, 1972, now abandoned.

BACKGROUND OF THE INVENTION

1. Field of the Invention

This invention has to do with a method for preparing vanadium-phosphorus-zirconium catalysts with good activity and selectivity and high physical strength for the oxidation of alkanes, cycloalkanes and mixtures rich therein to dicarboxylic acid anhydrides, particularly butane to maleic anhydride.

2. Description of the Prior Art

Vanadium-phosphorous complex catalysts for the oxidation of butane to maleic anhydride, are described in U.S. Pat. No. 3,293,268. Such catalysts operate at temperatures greater than 500°C. In general, yields of maleic anhydride with such catalysts are relatively low and not commercially attractive or feasible.

More recently, catalysts comprising antimony, molybdenum and iron or vanadium, have been described for oxidizing $C_4$ and $C_5$ paraffin hydrocarbons to maleic anhydride. The catalysts are indicated to be useful at 300°–600°C.

Metal-promoted vanadium-phosphorus complex catalysts are described in U.S. Pat. No. 3,156,705. The metal promoters, identified as phosphorus stabilizers, are broadly disclosed to include transition metals and rare earth metals. The catalysts are taught for oxidizing an olefin (butene) to a dicarboxylic acid anhydride (maleic anhydride). There is no teaching that such catalysts are effective in the more difficult oxidation of saturated hydrocarbons (alkanes and cycloalkanes).

In application Ser. No. 261,030, filed June 8, 1972, now abandoned, there is described an improved process for oxidizing an alkane to a dicarboxylic acid anhydride in the presence of a catalyst comprising a complex reaction product of a vanadium oxy salt and a phosphoric acid promoted with one or more of Cr, Fe, Hf, Zr, La and Ce. The atomic ratio of P/V is between about 0.5 and about 2, and the atomic ratio of promoter metal/V is between about 0.0025 and about 1, in such catalysts.

As an improvement over, and an extension of, the catalysts described in said application Ser. No. 461,777, now U.S. Pat. No. 3,888,886, the present invention is concerned with a particular method for making V/P/Zr catalysts and with the particular catalysts obtained with that method. In prior catalyst preparation methods using HCl, at least 5 moles or more of HCl were required per gram atom of vanadium. Such preparation method presents a high corrosivity problem requiring the use of expensive corrosion resistant equipment. It also increases the volume of material that must be handled. The method of this invention, however, does not involve the use of hydrogen halide (HCl) and eliminates problems associated with its use. When the vanadium or zirconium source or both, is a halogen-containing vanadium or zirconium salt or both, the amount of by-product hydrogen halide encountered is relatively and comparatively small and involves a relatively negligible problem.

SUMMARY OF THE INVENTION

In accordance with the present invention, there is provided a method for preparing vanadium-phosphorus-zirconium composites which are catalytically active and selective for the oxidation of an alkane, cycloalkane or mixtures thereof to a dicarboxylic acid anhydride and which have high physical strength. The method comprises forming an aqueous mixture of a vanadium compound and a lower dialkyl phosphonate, adding a zirconium salt, and then adding phosphoric acid or a compound which hydrolyzes to phosphoric acid to the resulting solution to form a slurry and drying the slurry.

The invention is also concerned with a process for oxidizing an alkane, cycloalkane or mixtures rich in them to a dicarboxylic acid anhydride by contacting the alkane with a molecular oxygen-containing gas under specified conditions in the presence of said composites.

DESCRIPTION OF SPECIFIC EMBODIMENTS

The catalysts produced by the method of this invention are effective in the oxidation of alkanes, cycloalkanes, and mixtures rich in alkanes and cycloalkanes to maleic anhydride in good yields and with good selectivity. These catalysts also have the high physical strength needed to be used in fluid bed reactors.

Preferably and in order to have all the aforementioned properties of activity, selectivity, and strength, the catalyst is prepared in three steps or stages. First, an aqueous slurry of vanadium pentoxide and a lower dialkyl phosphonate is refluxed at 100°–120°C for between about 0.5 hour and about 5 hours. Then, a zirconium salt is added and refluxing is continued for another 0.5 hour to 5 hours. Finally, phosphoric acid or a compound hydrolyzable to phosphoric acid is added and refluxing is continued (between about 0.5 hour and about 5 hours).

Vanadium compounds employable herein are $V_2O_5$, $VOCl_3$, $VO(NO_3)_3$, $NH_4VO_3$, and $VF_5$, of which $V_2O_5$ is particularly preferred. The zirconium salts are illustrated by $ZrOCl_2.4H_2O$, $ZrOCl_2.8H_2O$, $ZrO(OAc)_2.H_2O$, $ZrCl_4$, $Zr(OAc)_4$, $Na_2ZrCl_6$ and $ZrOBr_2.XH_2O$.

The phosphorus component of the catalyst of this invention is derived from both the lower dialkyl phosphonate and phosphoric acid. The lower dialkyl phosphonates have 1–4 carbon atoms in each alkyl group and include dimethyl phosphonate, diethyl phosphonate, dipropyl phosphonate, diisopropyl phosphonate, dibutyl phosphonate, diisobutyl phosphonate, di-t-butylphosphonate, and mixed esters, such as methyl ethyl phosphonate, methyl propyl phosphonate, and ethyl butyl phosphonate. These phosphonates can exist in one or both tautomeric forms:

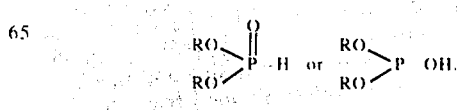

The corresponding trialkyl phosphites are readily hydrolyzed during the catalyst preparation to form dialkyl phosphonates. Accordingly, they are the equivalent of the dialkyl phosphonate and as such their use in the method of this invention is contemplated. The other phosphorus source is phosphoric acid or a phosphorus compound hydrolyzable to phosphoric acid, such as $P_2O_5$ and $POCl_3$. The concentration of phosphoric acid can be from about 25% to 100%.

The amount of phosphorus in the finished catalyst should be sufficient to give a phosphorus/vanadium atomic ratio of 1.1–1.5/1. The P/V atomic ratio attributable to the lower dialkyl phosphonate should be about 0.5/1, i.e., there will be used 0.5 gram atom of lower dialkyl phosphonate per gram atom of vanadium compound. Accordingly, there will be used between about 0.6 gram atom and about 1 gram atom of phosphoric acid per gram atom of vanadium compound. A P/V atomic ratio of about 1.2/1 is preferred.

The quantity of zirconium salt employed is from about 0.0025 to about 0.5 gram atom per gram atom of vanadium compound. Thus, the quantities of vanadium compound and zirconium salt are such that the atomic ratio of Zr/V of the final composite is between about 0.0025 and about 0.5.

The solution formed with the final step addition of phosphoric acid is refluxed, to form a slurry. Then, the slurry is concentrated and evaporated to substantially dry condition in trays or by spray drying. The dried material is ground to about 20–60 mesh (U.S. sieve size) for fixed bed operation. The ground material can be pelletized, for example, to ⅛ inch × 5/32 inch cylindrical pellets. Optionally, a binder such as stearic acid, can be added before pelletizing. Alternatively, the catalyst solution, before drying, can be used to impregnate a suitable carrier, such as alumina, alundum, silica, silicon carbide, silica-alumina, zirconia, zirconium phosphate, and/or a zeolite, to produce a supported catalyst suitable for use in a fixed or fluidized bed reactor. As a further and preferred alternative, the dried, unsupported catalyst can be ground to produce a powdered catalyst (e.g., 60–200 mesh) for use in a fluidized bed reactor.

The catalyst can be conditioned in the reactor by passing a hydrocarbon-air mixture through the catalyst bed at about 450°C., prior to running the oxidation reaction. Such conditioning is, however, not necessary to obtain catalyst efficiency. In practice, anhydride product can be obtained upon commencing the flow of oxidation feed through the reactor.

The charge stocks utilizable in the process using the catalyst of this invention are alkanes having between 4 and 10 carbon atoms, or mixtures of hydrocarbons rich in alkanes and cycloalkanes having between four and 10 carbon atoms. The alkanes can be normal alkanes or they can have branching. Typical alkanes are butane, pentane, isopentane, hexane, 3-methylpentane, heptane, octane, isooctane, and decane. The cycloalkanes utilizable can be methyl substituted and include cyclobutane, cyclopentane, methylcyclopentane, cyclohexane, methylcyclohexane, 1,4-dimethylcyclohexane, cycloheptane, and cyclooctane. Mixtures of hydrocarbons rich in alkanes and cycloalkanes having between four and 10 carbon atoms, i.e., containing about 70 weight per cent or more alkanes and cycloalkanes, are well known in the art. Particularly suitable and readily available mixtures are naphthas obtained from paraffinic or naphthenic petroleum sources. Full boiling range naphthas (boiling within the range of about 35°–230°C.) can be used but it is preferred to use light naptha cuts boiling within the range of about 35°–145°C. The naphthas usually contain about 5–15 per cent benzene and alkylbenzenes. It has been found that benzene is oxidized to maleic anhydride in the process of this invention, whereas to some extent alkylbenzenes are oxidized to benzene carboxylic acids or anhydrides. It will be understood that other mixtures can be used, such as a paraffinic raffinate from the glycol-water solvent extraction of reformates (Udex process).

Butane, because of its ready availability, is preferred. In the following discussion and exemplification, therefore, butane is used in most examples to demonstrate (but not to limit) the present process for producing maleic anhydride. It is contemplated that mixtures rich in butane can be used, such as a typical butane-butene (B-B) refinery stream.

The oxidation of n-butane (or other feed as aforedefined) to maleic anhydride is carried out using air or other molecular oxygen-containing gases, such as mixtures of carbon dioxide and oxygen or mixtures of nitrogen or steam with air or oxygen. Air is preferred. The oxidation reaction is carried out at temperatures of 300°–600°C., preferably 325°–550°C. The feed concentration is 0.5–6 volume percent butane in the oxygen-containing gas and preferably 1–5 volume percent. The contact time is generally varied between about 0.08–3 seconds, preferably about 0.16–1.6 seconds for fixed bed operation. Generally, contact times of up to about 30 seconds can be used in the case of fluidized bed operation. Thus contact time, depending upon the type of operation, will be about 0.08–30 seconds. Although the reaction can be carried out at 0.5–20 atmospheres pressure (absolute), it is preferably carried out at about 1–5 atmospheres. The reaction can be carried out in any suitable reactor for effecting vapor phase oxidation reactions. For example, a fixed catalyst bed can be employed. The reaction can be carried out, preferably, by using smaller catalyst particles in a fluidized reactor bed.

In the examples and tables, percent yield of "MA" indicates maleic anhydride yield expressed as weight of desired product based upon weight of (butane) feed and was determined by titration.

Similarly, selectivity to maleic anhydride is represented by:

$$\frac{\text{moles of maleic anhydride product}}{\text{moles of (hydrocarbon) feed reacted}} \times 100.$$

Contact time is determined by:

$$\frac{\text{quiescent catalyst bed volume}}{\text{volumetric flow rate at reactor temperature and pressure}}.$$

The flow rates of air and butane were measured at room temperature and pressure.

The attrition index (A.I.) is a relative rating of the per cent fines produced from the catalyst under test compared to the fined produced from a commercial vanadium sulfate (about 3%) on silica gel catalyst (Grace No. 906) used in a fluid process for oxidizing naphthalene to phthalic anhydride. The per cent fines is determined in 1 inch I.D. copper tube fluid bed apparatus provided at the top with a disengaging section adapted to retain particles of 40 microns or greater in diameter and provided with a thimble to entrap smaller size particles, i.e., fines. In operation, a weighed sample (about 20 ml.) of catalyst is placed in the fluid bed apparatus and the thimble is tared. Air is passed upwardly through the bottom of the tube at a rate of 13 liters per minute. After 1 hour, the air flow is stopped and the tared thimble is weighed to determine the weight of fines. The per cent of fines is calculated.

$$\% \text{ fines} = \frac{\text{g. of fines collected}}{\text{g. of catalyst charged}} \times 100.$$

$$\text{Attrition Index (A.I.)} = \frac{\% \text{ fines from test catalyst}}{\% \text{ fines from commercial catalyst}}$$

The invention is shown by the following illustrative examples, contrasted with comparative examples.

EXAMPLE 1

A vanadium-phosphorus-zirconium catalyst having a V-P-Zr ratio of 1/1.2/0.132 (atomic) was prepared as follows: 129.2g. of $V_2O_5$ and 78.1 g. of dimethyl phosphonate were added to 500 ml. of $H_2O$. The mixture was refluxed for 4 hours, followed by addition of 44.8 g. of $ZrO(OAc)_2.H_2O$. Reflux was continued for 80 minutes during which time the slurry turned blue. To the slurry, 114 g. of 85% $H_3PO_4$ was added. Reflux was continued for an additional 2 hours. The mixture was put into a tray in an oven to dry at 130°C. The resulting solid was ground to 60–200 mesh.

The catalyst (100 ml.) was charged to a fluid bed reactor at room temperature and 20 m./min. of n-butane and 1,000 ml./min. of air were passed through the catalyst. The reactor was heated at 450°C for about 16 hours.

A mixture of 30 ml./min. of n-butane and 750 ml./min. of air was passed through the catalyst at 425°C. Maleic anhydride was determined by scrubbing the exit gases through water, followed by titration of an aliquot of the aqueous solution. In a 1 hour sampling period, 73% MA yield was obtained at 57% butane selectivity. At 400°C., the MA yield was 54% at 60% butane selectivity.

The physical stability of the catalyst was determined in an accelerated attrition test and compared to a commercial fluid bed catalyst in the same test. Its attrition index (A.I.) was 0.7. This shows the catalyst to be superior to the commercial catalyst in physical stability.

EXAMPLE 2

A vanadium-phosphorus-zirconium catalyst having a V-P-Zr ratio (atomic) of 1/1.7/0.132 was prepared as follows: 129.2g. of $V_2O_5$ and 78.1 g. of dimethyl phosphonate were added to 500 ml. of $H_2O$. The mixture was refluxed for four hours, followed by addition of 44.8 g. of $ZrO(OAc)_2.H_2O$. Reflux was continued for 80 minutes, followed by addition of 196.6g. of 85% $H_3PO_4$. Reflux was continued for an additional 2 hours. The mixture was put into a tray in an oven to dry at 130°C. The resulting solid was ground to 60–200 mesh.

The catalyst (100 ml.) was charged to a fluid bed reactor at room temperature and 20 ml./min. of butane and 1,000 ml./min. of air were passed through the catalyst. The reactor was heated at 450°C. for about 16 hours.

A mixture of 30 ml./min. of n-butane and 750 ml./min. of air was passed through the catalyst at 450°C. Maleic anhydride was determined by scrubbing the exit gases through water, followed by titration of an aliquot of the aqueous solution. In a 1 hour sampling period, 46% MA yield was obtained at 51% butane selectivity. Example 2 demonstrates that the phosphorus from the reducing agent becomes part of the catalyst composition. The amount of $H_3PO_4$ used in this example is what is used in preparations done in HCl, in which all phosphorus came from $H_3PO_4$. As a result, the amount/$H_3PO_4$ charged has to be reduced by the amount of dimethyl phosphonate used in order to obtain a catalyst with the proper composition.

EXAMPLE 3

A vanadium-phosphorus-zirconium catalyst having a V-P-Zr of 1/1.2/0.132 (atomic) was prepared as follows: 129.2 g. of $V_2O_5$, 78.1 g. of dimethyl phosphonate and 44.8 g. of $ZrO(OAc)_2.H_2O$ were added to 550 ml. of $H_2O$. The mixture was refluxed for 5 hours and 20 minutes followed by the addition of 114 g. of 85% $H_3PO_4$. The mixture was refluxed for an additional hour. The mixture was put into a tray in an oven to dry at 130°C. The resulting solid was ground to 60–200 mesh.

The catalyst (100 ml.) was charged to a fluid bed reactor at room temperature and 20 ml./min. of butane and 1,000 ml./min. of air were passed through the catalyst. The reactor was heated at 450°C for about 16 hours.

A mixture of 30 ml./min. of n-butane and 750 ml./min. of air was passed through the catalyst at 400°C. Maleic anhydride was determined by scrubbing the exit gases through water, followed by titration of an aliquot of aqueous solution. In a 1-hour sampling period, 32% MA yield was obtained at 50% butane selectivity.

The physical stability of the catalyst was determined in an accelerated attrition test. The attrition index (A.I.) was 0.9.

EXAMPLE 4

A vanadium-phosphorus-zirconium catalyst having a V-P-Zr ratio of 1/1.2/0.132 (atomic) was prepared as follows: 129.2 g. of $V_2O_5$, 78.1 g. of dimethyl phosphonate and 114 g. of 85% $H_3PO_4$ was added to 550 ml. of $H_2O$. The mixture was refluxed for 4 hours, followed by the addition of 44.8 g. of $ZrO(OAc)_2.H_2O$. The mixture was refluxed an additional 1 ½ hours. The mixture was put into a tray in an oven to dry at 130°C. The resulting solid was ground to 60–200 mesh.

The catalyst (100 ml.) was charged to a fluid bed reactor at room temperature and 20 ml./min. of n-butane and 1,000 ml./min. of air were passed through the catalyst. The reactor was heated at 450°C for about 16 hours.

A mixture of 30 ml./min. of n-butane and 750 ml./min. of air was passed through the catalyst at 400°C. Maleic anhydride was determined by scrubbing the exit gases through water, followed by titration of an aliquot of the aqueous solution. In a one-hour sampling period, 56% MA yield was obtained at 64% butane selectivity.

The physical stability of the catalyst was determined in an accelerated attrition test. The attrition index (A.I.) was 1.5.

The effect of reagent addition order in the catalyst preparation is clearly demonstrated by the data obtained using the catalysts of Examples 1, 3, 4 and given in Table I. The data show that the preferred order of addition is vanadium + phosphonate, zirconium, and phosphorus (phosphoric acid) last. This gives a catalyst of superior physical hardness and high maleic anhydride yields.

Table I

| Reagent Addition Order | | | Example No. | % Maleic Anhydride Yield | % Butane Selectivity | A.I. |
|---|---|---|---|---|---|---|
| 1st | 2nd | 3rd | | | | |
| V | Zr | P | 1 | 54 | 60 | 0.7 |
| V,Zr | P | | 3 | 32 | 50 | 0.9 |
| V,P | Zr | | 4 | 56 | 64 | 1.5 |

Temperatures = 400°C., contact time = 3.3 sec. in all Examples.
V = vanadium compound + dimethyl phosphonate.
P = phosphorus as phosphoric acid.

EXAMPLE 5

A vanadium-phosphorus-zirconium catalyst having a V-P-Zr ratio (atomic) of 1/1.2/0.132 was prepared as follows: 129.2 g. of $V_2O_5$, 117.3 g. of dimethyl phosphonate and 40.4 g. of 85% $H_3PO_4$ was added to 500 ml. of $H_2O$. The mixture was refluxed for 4 hours, followed by the addition of 44.8 g. of $ZrO(OAc)_2.H_2O$. The mixture was refluxed an additional 2 hours. The mixture was put into a tray in an oven to dry at 130°C. The resulting solid was ground to 60–200 mesh.

The catalyst (100 ml.) was charged to a fluid bed reactor at room temperature and 20 ml./min. of n-butane and 1000 ml./min. of air were passed through the catalyst. The reaction was heated at 450°C for about 16 hours.

A mixture of 30 ml./min. of n-butane and 750 ml./min. of air was passed through the catalyst at 425°C. Maleic anhydride was determined by scrubbing the exit gases through water, followed by titration of an aliquot of the aqueous solution. In a 1-hour sampling period, 41% MA yield was obtained at 38% butane selectivity.

This example (compare to Example 4) demonstrates that the molar ratio of dimethyl phosphonate to $V_2O_5$ used should be approximately one. Higher ratios give catalysts which are not as selective.

EXAMPLE 6

The catalyst of Example 1 (250 ml.) was charged to a (36 inch long by 1 inch diameter) fluid bed reactor to test the catalyst at longer contact times.

A mixture of 30 ml./min. of n-butane and 750 ml./min. of air was passed through the catalyst at 400°C. Maleic anhydride was determined by scrubbing the exit gases through water, followed by titration of an aliquot of the aqueous solution. In a 1-hour sampling period, 79% MA yield was obtained at 59% butane selectivity.

EXAMPLE 7

The catalyst and reactor of Example 6 were used to oxidize light Arabian Naphtha in order to show the catalyst was applicable to other feeds. The light Arabian naphtha used was a boiling point cut of $C_5$ to 290°F., with an average molecular weight of about 100 and an average carbon number of seven. It contained about 70 wt. % paraffins, 18% monocycloparaffins, < 1 wt. % olefins, and 12% alkylbenzenes.

A mixture of 6.4 ml./hour of liquid light Arabian naphtha and 1,000 ml./min. of air was passed through the catalyst at 400°C. Maleic anhydride was determined by scrubbing the exit gases through water, followed by titration of an aliquot of the aqueous solution. In a 1-hour sampling period, 55% MA yield was obtained at about 56% selectivity to maleic anhydride.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for preparing a vanadium-phosphorus-zirconium catalyst composite that consists essentially of:
    a. forming an aqueous mixture of $V_2O_5$, $VOCl_3$, $VO(NO_3)_3$, $NH_4VO_3$, or $VF_5$ and a lower dialkyl phosphonate, in a P/V atomic ratio of 0.5, refluxing said mixture for between about 0.5 hour and 5 hours;
    b. adding $ZrOCl_2.4H_2O$, $ZrOCl_2.8H_2O$, $ZrO(OAc)_2.H_2O$, $ZrCl_4$, $Zr(OAc)_4$, $Na_2ZrCl_6$, or $ZrOBr_2.XH_2O$, in a Zr/V atomic ratio of between about 0.0025 and about 0.5, continuing refluxing for between about 0.5 hour and about 5 hours;
    c. adding phosphoric acid or a compound hydrolyzable to phosphoric acid, in a P/V atomic ratio of between about 0.6 and about 1, continuing refluxing for between about 0.5 hour and about 5 hours to form a slurry; and
    d. drying said slurry.

2. The method of claim 1, wherein said lower dialkyl phosphonate is dimethyl phosphonate.

3. The method of claim 1, wherein said zirconium salt is zirconyl acetate.

4. The method of claim 2, wherein said zirconium salt is zirconyl acetate.

* * * * *